US008173021B2

(12) United States Patent
Wolff et al.

(10) Patent No.: US 8,173,021 B2
(45) Date of Patent: May 8, 2012

(54) METHOD FOR THE PREPARATION OF SULFATED CELLULOSE MEMBRANES AND SULFATED CELLULOSE MEMBRANES

(75) Inventors: Michael Wolff, Biederitz (DE); Udo Reichl, Magdeburg (DE); Lars Opitz, Doellingen (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 111 days.

(21) Appl. No.: 12/580,413

(22) Filed: Oct. 16, 2009

(65) Prior Publication Data
US 2010/0093059 A1   Apr. 15, 2010

(51) Int. Cl.
*B01D 61/00* (2006.01)
*C08B 1/00* (2006.01)
*C08B 1/16* (2006.01)
*C07K 1/34* (2006.01)
*B01D 67/00* (2006.01)
*B01D 71/10* (2006.01)

(52) U.S. Cl. .............. 210/651; 210/645; 210/500.29; 435/239; 430/412; 430/413; 264/48; 536/56; 536/57

(58) Field of Classification Search .. 210/500.29–500.3, 210/500.37, 645, 650, 651; 264/48; 435/230; 530/412, 413; 536/56, 57
See application file for complete search history.

(56) References Cited

U.S. PATENT DOCUMENTS

| | | | | |
|---|---|---|---|---|
| 4,200,726 A * | 4/1980 | Ishii et al. | ............. | 528/99 |
| 4,851,120 A * | 7/1989 | Reineke et al. | ............. | 210/500.25 |
| 5,667,684 A * | 9/1997 | Motomura et al. | ............. | 210/506 |
| 5,734,025 A * | 3/1998 | Komai et al. | ............. | 530/417 |
| 6,951,933 B2 * | 10/2005 | West et al. | ............. | 536/123.1 |
| 8,003,363 B2 * | 8/2011 | Djurup et al. | ............. | 435/239 |
| 8,003,364 B2 * | 8/2011 | Post Hansen et al. | ......... | 435/239 |
| 2010/0119552 A1 * | 5/2010 | Hansen et al. | ............. | 424/232.1 |
| 2011/0306114 A1 * | 12/2011 | Post Hansen et al. | ......... | 435/239 |
| 2011/0312060 A1 * | 12/2011 | Djurup et al. | ............. | 435/239 |

FOREIGN PATENT DOCUMENTS

| | | |
|---|---|---|
| DE | 692029 | 4/1936 |
| WO | EP 0 053 473 | 11/1981 |
| WO | EP 0 171 086 | 8/1985 |
| WO | WO 99/31120 | 6/1999 |

OTHER PUBLICATIONS

Faber, R., et al., "Microporous membrane adsorbers: basic concepts and recent developments", Desalination 199, 2006. pp. 553-554.
Zon, H., et al., "Affinity membrane chromatography for the analysis and purification of proteins", Journal of biochemical and biophysical methods 49, 2001 pp. 199-240.
va Reis, R., et al., "Membrane separation in biotechnology", Current Opinion in Biotechnology, 2001. pp. 208-211.
Chen, C. et al., "Purification of capsid-like particles of infectious bursal disease virus (IBDV) VP2 expressed in *E. coli* with a metal-ion affinity membrane system", Journal of Virologial methods, Jul. 2005. pp. 51-58.
Salm, M. A., et al., "Sulphation of Jute Cellulos", Indian Chem Soc., vol. LT, Mar. 1974. pp. 433-436.
Heinze, T., et al., "New Polymers Based on Cellulose", Institue of Organic Chemistry and Macromolecular Chemistry, Friedrich Schiller University of Jena, Germany. pp. 39-44.

* cited by examiner

*Primary Examiner* — Ana Fortuna
(74) *Attorney, Agent, or Firm* — Whitham Curtis Christofferson & Cook, PC

(57) ABSTRACT

The present invention relates to methods for the preparation of functionalized sulfated cellulose membranes. In particular, the present invention relates to the preparation of sulfated cellulose membranes under specific reaction conditions allowing to provide a sulfated cellulose membrane useful for pseudo-affinity purification. In another aspect, the present invention relates to the sulfated cellulose membrane itself as well as its use for isolation of proteinaceous compositions. Finally, the present invention provides a method for isolating whole virus, virus proteins or heparin binding molecules comprising the step of affinity purification using the sulfated cellulose membrane according to the present invention.

18 Claims, No Drawings

METHOD FOR THE PREPARATION OF SULFATED CELLULOSE MEMBRANES AND SULFATED CELLULOSE MEMBRANES

The present invention relates to methods for the preparation of functionalized sulfated cellulose membranes. In particular, the present invention relates to the preparation of sulfated cellulose membranes under specific reaction conditions allowing to provide a sulfated cellulose membrane useful for pseudo-affinity purification. In another aspect, the present invention relates to the sulfated cellulose membrane itself as well as its use for isolation of proteinaceous compositions. Finally, the present invention provides a method for isolating whole virus, virus proteins or heparin binding molecules comprising the step of affinity purification using the sulfated cellulose membrane according to the present invention.

TECHNOLOGICAL BACKGROUND

Isolation of whole virus and viral proteins is of most importance for the production of vaccines useful as prophylactic or therapeutic vaccines against viral infections. Typically, the immune response elicited by virus vaccines is based on raising an appropriate cellular and humoral immunity against immunogenes of the virus. For example, for influenza virus, the envelope proteins or surface proteins neuraminidase (NA), hemagglutinin (HA) and the ion channel (M2) are regarded as the most prominent candidate vaccines. In case of e.g. HIV gp120 and gep41 are assumed to represent vaccine candidates.

Influenza infection is a wide spread contagious disease of the respiratory tract. Due to annual death rates and its potential to cause pandemics, influenza remains a major public health concern. To control influenza outbreaks prophylactic vaccinations in conjunction with anti-viral medications are regarded as being most promising.

The same is true for vaccinia virus infection. To control or eradicate new outbreaks of vaccinia virus and other small pox virus, prophylactic vaccinations are required.

Influenza and small pox are two severe infectious diseases that can lead to death. Vaccine doses are currently produced for both diseases. While several million humans are getting annually vaccinated against influenza, the vaccinia virus vaccines are produced to be stocked in case of an emerging pandemic.

Today efforts are undertaken to switch from conventional vaccine production processes, e.g. virus production in primary cell lines (for vaccinia virus) or embryonated hen's egg (for influenza virus), to continuous cell line cultures. However, these require new downstream processing strategies allowing isolation and purification of the whole virus or virus components, in particular, of viral membrane proteins which are the main immunogens of the virus. Various approaches have been suggested for purification of whole virus and virus proteins. For example, WO 96/15231 provides a general overview of methods useful for producing biologicals in protein free cultures. Said methods comprise pseudo-affinity purification steps as well as other chromatography methods, enzyme treatment steps, ultra-filtration step and hydrophobic interaction steps.

In EP 171 086 a method for purification of influenza virus is disclosed. Said method comprises subjecting a solution containing the influenza virus to column chromatography using, as a gel for a chromatography, a sulfuric acid ester of cellulose or a cross-linked polysaccharide.

In said document, the modification and functionalization of a chromatography gel useful for pseudo-affinity column chromatography for influenza virus is described. The gel is a sulfuric acid ester of cellulose or a cross-linked polysaccharide. The steps for functionalization of the cellulose comprises reacting pyridine with chloro-sulfonic acid at a temperature below 0° C., thereafter heating said mixture to a temperature of about 65 to 70° C. and maintaining said temperature while adding the crystalline cellulose gel and stirring the mixture for another three hours at a temperature of about 65 to 70° C. Thereafter, the mixture is cooled, neutralized and a gel is obtained useful for column chromatography.

However, major drawbacks of applying column chromatography with cellulose gel include long process time with large recovery liquid volume. In addition, the flow rates of the column chromatography are limited. Further, the preparation of the columns is time consuming and cumbersome and requires regeneration steps. Thus, the state of the art method of an unit operation often used in influenza-purification comprising column chromatography based on the sulfated cellulose gel, known as Cellufine™ sulfate has major disadvantages due to the limited flow rate in view of the high backpressure, thus, leading to sub-optimal productivity rates of the process.

It is therefore an object of the present invention to provide a method for purification of whole virus or virus proteins in a simple manner overcoming the drawbacks in the art.

It is another object of the present invention to provide material useful for said purification, namely to provide material useful for pseudo-affinity purification of virus and viral proteins.

SUMMARY OF THE PRESENT INVENTION

In a first aspect, the present invention relates to a method for the preparation of sulfated cellulose membranes, said method comprises the steps of:
a) adding chloro-sulfonic acid to pyridine at a temperature below or equal to 0° C.;
b) reacting said mixture at a temperature of 60° C. or above;
c) cooling the mixture at a temperature of 40° C. or below;
d) adding cellulose membrane to said mixture and
e) reacting the same at a temperature of 40° C. or below to obtain a sulfated cellulose membrane.

Particularly preferred, the cellulose membrane is a regenerated cellulose membrane, in particular, the cellulose membrane is a reinforced cellulose membrane.

In another aspect, the present invention relates to sulfated cellulose membrane obtainable with a method according to the present invention. In a preferred embodiment, the sulfated cellulose membrane has a degree of sulfation of cellulose in the range of from 0.5 to 15% based on the cellulose.

In another aspect, the present invention provides a method for isolating whole virus or virus proteins comprising the steps of affinity purification using the sulfated cellulose membranes according to the present invention. Said method is particularly useful for isolating whole virus.

DETAILED DESCRIPTION OF THE PRESENT INVENTION

In a first embodiment, the present invention relates to a method for the preparation of sulfate cellulose membranes, comprising the steps of:
a) adding chloro-sulfonic acid to pyridine at a temperature below or equal to 0° C.;
b) reacting said mixture at a temperature of 60° C. or above;

c) cooling the mixture at a temperature of 40° C. or below;
d) adding cellulose membrane to said mixture and
e) reacting the same at a temperature of 40° C. or below to obtain a sulfated cellulose membrane.

That is, treating cellulose membranes under the specific conditions mentioned above, it is possible to provide membranes allowing effective, fast and reliable isolation and purification of whole virus and virus proteins from a material containing the same. The present invention is based on the finding that under specific reaction conditions, it is possible to functionalize, e.g. to sulfate cellulose membranes, thus, providing sulfated cellulose membranes allowing highly effective purification of whole virus and virus proteins.

The starting cellulose membranes are commercially available, for example, membrane filters from Whatman and Sartorius.

The sulfation of the cellulose membrane is conducted with a sulfating agent, such a chloro-sulfonic acid or anhydrous sulfuric acid in an organic solvent, like pyridine.

The degree of sulfation (content of the sulfonyl group) of cellulose is usually in the range of from 0.5 to 15% based on the cellulose. Preferably, the degree of sulfation of cellulose is 1.0% to 10%, like 2% to 6% based on the cellulose.

The modified cellulose membranes claimed herein achieved high product recoveries while reducing contaminants. Further, the retention time in the filter is reduced compared to the retention time in the column used for affinity purification. Hence, the productivity can be significantly enhanced since the flow rate can be increased due to a reduced back pressure and the binding kinetics are approved.

Preferably, the method according to the present invention additionally contains the step of cooling the reaction mixture after reacting the cellulose membrane with the mixture of chloro-sulfonic acid and pyridine to ambient temperature. Further preferred, the method additionally comprises the step of neutralising the reaction mixture with a base. Said base is preferably an aqueous sodium hydroxide solution.

The method of the present invention for the preparation of sulfated cellulose membranes may additionally comprise the step of washing the obtained sulfated cellulose membrane with a suitable buffer, e.g. with phosphate buffered saline solution in order to provide a sulfated cellulose membrane ready for use. The sulfated cellulose membrane may be stored in phosphate buffered saline solution or 20% ethanol. Alternatively, the sulfated cellulose membrane according to the present invention is dried for storage.

As outlined above, the reaction between chloro-sulfonic acid or anhydrous sulfuric acid in an organic solvent, like pyridine, is conducted at a temperature of 60° C. or above, preferably at a temperature of from 60° C. to 80° C., like 60° C. to 70° C., in particular, about 65° C.

After reacting the mixture of pyridine and chloro-sulfonic acid, said mixture is cooled at a temperature of 40° C. or below, for example at a temperature in the range of from 40° C. to 10° C., like 40° C. to 20° C., in particular, 40° C. to 30° C. Further, the temperature for reacting the mixture of pyridine and chloro-sulfonic acid with the cellulose membrane, in particular, the regenerated cellulose membrane, like a reinforced cellulose membrane, is below 40° C. Preferably, the temperature is in the range of from 40° C. to 10° C., like 40° C. to 20° C., in particular, 40° C. to 30° C., more preferred 40° C. to 35° C.

It is important that the temperature of the reaction mixture does not exceed the range mentioned above when adding the cellulose membrane. Temperatures above 60° C., in particular, above 65° C. would cause destruction of the membrane and membrane structure. Thus, it is not useful to add the cellulose material, namely the cellulose membrane to the reaction mixture of pyridine and chloro-sulfonic acid or anhydrous sulfuric acid when the temperature of said reaction mixture is above 60° C., preferably above 65° C.

In a further embodiment of the present invention, a sulfated cellulose membrane obtainable with a method according to the present invention is provided. Preferably, the sulfated cellulose membrane has a degree of sulfation of the cellulose in the range of from 0.5 to 15% based on the cellulose. Preferably, said sulfation degree is in the range of from 1.0 to 10%, like 2 to 6% based on the cellulose.

In a preferred embodiment, said sulfated cellulose membrane is obtained using a regenerated cellulose membrane, in particular, a reinforced cellulose membrane.

The sulfated cellulose membrane allows to purify whole virus or virus components, in particular, virus proteins, like virus membrane proteins.

Compared to the prior art gel of a sulfuric acid ester of cellulose, for example, known as Cellufine™ sulfate, the membranes according to the present invention are allowed to be used at higher pressures. That is, the gel used in a column chromatography may be run with a pressure of 2 bar at most while the membranes according to the present invention may allow to conduct purification at pressures of up to 3 times higher, e.g. at 6 bar or more.

In addition, the flow rate can be increased. While e.g. using column chromatography (Tricom5/150, GE-Healthcare) containing Cellufine™ sulfate resin allow flow rates of 0.5 ml per minute at most, membranes according to the present invention may allow flow rates of up to 20 ml per minute. The modified membranes achieved high productive recoveries and contaminant reduction. Due to a fast binding kinetic and a low back pressure, membrane absorbers according to the present invention enable to operate the capturing process at an increased flow rate. Hence, the productivity can be significantly enhanced making them to available choice for industrial vaccine production processes.

In addition, the retention time of the compounds to be isolated, e.g. the whole virus or viral components in the membrane is reduced compared to the retention time in the column of the prior art technique using a cellulose based gel.

That is, the advantages of applying membranes of the present invention compared with the gel based column chromatography known in the art are:
i) low process time,
ii) low recovery liquid volume,
iii) higher flow rates possible,
iv) lower pressure drop,
v) ease of scale up,
vi) ease of validation.

The membranes may be designed to represent disposable membranes to be used in commonly known membrane holders, e.g. stainless steel membrane holders.

In a further aspect, the present invention relates to the use of the sulfated cellulose membranes according to the present invention for isolating proteinaceous compositions. In particular, said proteinaceous compositions are whole virus or fragments thereof. Thus, in another embodiment, the present invention relates to the use of sulfated cellulose membranes according to the present invention for the purification of compositions containing virus and/or non-virus proteins. Preferably, said use relates to the isolation of whole influenza virus or whole vaccinia virus or proteinaceous fragments thereof.

Finally, the present invention relates to a method for isolating whole virus or virus proteins comprising the step of pseudo-affinity purification using the sulfated cellulose membranes obtainable according to the method of the present invention.

In addition, the membranes according to the present invention are also suitable for the purification of heparin binding molecules not derived from virus. For example, the membranes according to the present invention may be used for the purification of heparin binding EGF-like growth factor, antithrombin, heparin binding growth factor 8 and serpins.

The following examples illustrate the invention further without limiting the same to the specific embodiment described in the examples.

EXAMPLES

Preparation Example

The sulphated reinforced cellulose membrane for the membrane adsorption chromatography is obtained as follows:

To 20 ml pyridine, chloro-sulfonic acid (1.12 ml) is added dropwise below or at 0° C. After the addition, the mixture is heated to 65° C. while stirring and than cooled to 35° C. to 40° C. 30 regenerated cellulose membranes (RC 55 membrane filter, 25 mm diameter, Whatman) are added to the cooled raction mixture and the reaction is continued under stirring at 35° C. to 40° C. for 12 hours. After the reaction, the mixture is cooled to room temperature and neutralized with aqueous sodium hydroxide. Subsequently, the membrane is washed well with PBS and stored in 20% ethanol or dried.

Example 1

Purification of the Viral Membrane Protein Hemagglutinin from Influenza

MDCK cells from ECACC, UK, Nr. 841211903 are initially grown in roller bottles (Greiner, Germany, 850 cm$^2$) containing 250 ml GMEM basal medium (Invitrogen/Gibco, #22100-093) supplemented with FCS. After the cells reach confluency they are washed with PBS, trypsinized and applied as an innoculum ((2-3)×10$^5$ cells/ml) for a 5 l bioreactor (B. Braun Biotech) containing the same media and 2.0 g/l Cytodex 1 solid microcarriers (Amersham Biosciences). The cells are cultivated under standard conditions for 4 days, washed with phosphate buffered saline (PBS) and infected with Influenza A Puerto Rico/8/34, H1N1 (NIBSC #99-716) at a MOI of 0.025. The infected cultures are maintained for 48 to 72 h in virus maintenance medium under standard conditions as described in Genzel et al., Vaccine, 2004, 22, 2202-2208. After cultivation, cells and microcarriers as well as cell agglomerates are separated from the medium by sedimentation. The sediment is than subjected to chemical inactivation with 12 mM β-propiolactone (Serva Electrophoresis) for 24 h at 37° C.

Then, polysorbate 80 (0.025%, w/v) and cethyltrimethylammonium bromide (0.05%, w/v) is added to the sediment and the mixture is incubated overnight at 4° C. while agitating to solubilize the viral membrane protein from the lipid membranes of the cellular and viral components.

Next, equimolar amounts of sodium cholate compared to cethyltrimethylammonium bromide are added to the mixture, thus, reducing the formation of micelles of the surfactants. The mixture is incubated for another 12 h at 4° C. while agitating.

Thereafter, the mixture is centrifuged for 10 min with 9000 g. Subsequently, the supernatant is diafiltrated against PBS using a membrane with a MWCO of 30,000 Da (Millipore) to concentrate the mixture and to remove salts and free surfactants.

Afterwards, the obtained solution is incubated with Amberlite XAD-4 to reduce the amount of surfactant. After performing the hydrophobic interaction chromatography with Amberlite XAD-4, the protein solution is centrifugated for 10 min at 9000 g.

The sample is loaded to 15 layers of the sulphated regenerated cellulose membranes in a stainless steel membrane holder (Whatman) with a flow rate of 0.5 ml/min in phosphate buffer containing 50 mM NaCl at room temperature. The target protein is eluted after a column wash (phosphate buffer containing 50 mM NaCl) with 1.2 M NaCl in PBS at room temperature.

The eluted fractions are pooled and diafiltrated against PBS using a membrane with a MWCO of 30,000 Da (Millipore) to remove salts. Alternatively, diafltration can be performed in a Vivaspin 1R Hydrosart with a MWCO of 30.000 Da (Sartorius) or the salts can be eliminated by a size exlusion chromatography e.g. Toyopearl (HW-55S).

Example 2

Purification of Whole Inactivated Virus

MDCK cells from ECACC, UK, Nr. 841211903 are initially grown in roller bottles (Greiner, Germany, 850 cm$^2$) containing 250 ml GMEM basal medium (Invitrogen/Gibco, #22100-093) supplemented with FCS. After the cells reach confluency they are washed with PBS, trypsinized and applied as an innoculum ((2-3)×10$^5$ cells/ml) for a 5 l bioreactor (B. Braun Biotech) containing the same media and 2.0 g/l Cytodex 1 solid microcarriers (Amersham Biosciences). The cells are cultivated under standard conditions for 4 days, washed with PBS and infected with Influenza A Puerto Rico/8/34, H1N1 (NIBSC #99-716) at a MOI of 0.025. The infected cultures are maintained for 48 to 72 h in virus maintenance medium under standard conditions as described in Genzel et al., Vaccine, 2004, 22, 2202-2208. After cultivation, cells and microcarriers as well as cell agglomerates are separated from the medium by sedimentation. The cultivation broth is than clarified by a combination of two filters (pore size: 5 and 0.65 μm, GE Water & Process Technologies) and subjected to chemical inactivation with 3 mM β-propiolactone (Serva Electrophoresis) for 24 h at 37° C. The inactivated broth is again clarified by a 0.45 μm membrane filter (GE Water & Process Technologies) and approximately 20-fold concentrated by a cross flow ultrafiltration (750 kDa; GE-Healthcare).

The concentrate is subjected to 15 layers of the sulphated reinforced cellulose membranes in a stainless steel filter holder (Pall) with a flow rate of 15 ml/min at room temperature in phosphate buffer containing 50 mM NaCl. The virus is eluted after a column wash with phosphate buffer containing 0.6 M NaCl at room temperature.

The eluted fractions are pooled and diafiltrated against PBS using a membrane with a MWCO of 30,000 Da (Millipore) to remove salts.

The final chromatography step is based on the EEL-polymer affinity chromatography. The diafiltrated virus from the sulphated reinforced cellulose membrane chromatography is loaded to a 3 ml EEL-polymer (Galab Technology GmbH) with a flow rate of 0.2 ml/min at 4° C. or at room temperature. The virus is eluted after a column wash with 0.5 M lactose in column loading buffer with a flow rate of 0.5 ml/min at 4° C. or at room temperature.

The eluted fractions are pooled and diafiltrated against phosphate buffered saline (PBS) using a membrane with a MWCO of 30,000 Da (Millipore) to remove lactose and salts. Alternatively, diafiltration can be performed in a Vivaspin 1R Hydrosart with a MWCO of 30.000 Da (Sartorius).

Example 3

Purification of Whole Inactivated Virus

As example 2 but without the EEL chromatography and the subsequent lactose removal step.

Example 4

Purification of Heparin Binding Molecules with a Sulfated Reinforced Cellulose Membrane Filter Heparin binding molecules from cell culture, blood, serum or other sources can be captured or concentrated by a sulfated reinforced cellulose membrane.

Human serum is diluted 1:20 and subjected to 15 layers of the sulphated regenerated cellulose membranes (prepared as described in example 6) in a stainless steel membrane holder (Whatman) with a flow rate of 0.2 ml/min at room temperature. Nonbinding proteins are eluted from the membrane with a flow rate of 0.2 ml/min PBS at room temperature. The binding proteins are than eluted by a linear gradient from 0 to 2 M NaCL and monitored with an online absorbance measurement at 280 nm. Individual peaks are dialysed against PBS and analysed by peptide mass fingerprint LC-MS.

Example 5

Comparison of the Sulfated Cellulose Membrane According to the Present Invention with Prior Art Membrane Absorber MDCK cells from ECACC, UK, Nr. 841211903 are initially grown in roller bottles (Greiner, Germany, 850 cm$^2$) containing 250 ml GMEM basal medium (Invitrogen/Gibco, #22100-093) supplemented with FCS. After the cells reach confluency they are washed with PBS, trypsinized and applied as an inocculum ((2-3)×10$^5$ cells/ml) for a 5 l bioreactor (B. Braun Biotech) containing the same media and 2.0 g/l Cytodex 1 solid microcarriers (Amersham Biosciences). The cells are cultivated under standard conditions for 4 days, washed with PBS and infected with Influenza A Puerto Rico/8/34, H1N1 (NIBSC #99-716) at a MOI of 0.025. The infected cultures are maintained for 48 to 72 h in virus maintenance medium under standard conditions as described in Genzel et al., Vaccine, 2004, 22, 2202-2208. After cultivation, cells and microcarriers as well as cell agglomerates are separated from the medium by sedimentation. The cultivation broth is than clarified by a combination of two filters (pore size: 5 and 0.65 μm, GE Water & Process Technologies) and subjected to chemical inactivation with 3 mM β-propiolactone (Serve Electrophoresis) for 24 h at 37° C. The inactivated broth is again clarified by a 0.45 μm membrane filter (GE Water & Process Technologies) and approximately 20-fold concentrated by a cross flow ultrafiltration (750 kDa; GE-Healthcare).

The concentrate is loaded to 15 layers of the sulphated regenerated cellulose membranes in a stainless steel membrane holder (Whatman) with a flow rate of 0.5 ml/min in phosphate buffer containing 50 mM NaCl at room temperature. The virus is eluted after an adsorber wash (phosphate buffer containing 50 mM NaCl) with 0.6 M NaCl in PBS at room temperature. Further adsorbed contaminants are eluted with 2 M NaCl in PBS at room temperature.

Same concentrate is loaded to cation exchange membrane adsorbers S75 and C75 (Sartorius AG) with a flow rate of 0.5 ml/min in phosphate buffer containing 50 mM NaCl at room temperature. The virus is eluted after an adsorber wash (phosphate buffer containing 50 mM NaCl) with 0.6 M NaCl in PBS at room temperature. Further adsorbed contaminants are eluted with 2 M NaCl in PBS at room temperature.

TABLE 1

Comparison of sulphated regenerated cellulose membrane with ion exchange membrane adsorbers S75 and C75 (LOQ - limit of quantification)

|  | double stranded DNA | | | HA activity | | | total protein content | | |
| --- | --- | --- | --- | --- | --- | --- | --- | --- | --- |
|  | C75 | S75 | sulphated membrane | C75 | S75 | sulphated membrane | C75 | S75 | sulphated membrane |
| Concentrate | 100 | 100 | 100 | 100 | 100 | 100 | 100 | 100 | 100 |
| Flow through | 29.9 | 44.3 | 50.2 | 37.5 | 14.4 | 21.4 | 47.6 | 47.5 | 49.1 |
| Eluted product | 40.1 | 38.8 | 10.1 | 63 | 75.7 | 81.6 | 16.1 | 18.7 | 16.4 |
| Further Elution | 16.3 | 5.9 | 23.2 | 1.5 | 1.5 | 1.5 | LOQ | LOQ | 4.7 |
| Summation | 86.3 | 89 | 83.5 | 102 | 91.6 | 104.5 | 63.7 | 66.2 | 70.2 |

Membrane absorbers C75 and S75 represents typical ion exchange membranes known in the art, from the results shown in the table above, it is clear that the sulfated cellulose membrane according to the present invention provides superior properties not only with respect to an increased double stranded DNA reduction, namely, host cell DNA reduction. Furthermore, the percentage of molecules having HA activity is increased in the eluate compared to the C75 and S75 membranes.

Example 6

Comparison of the Sulfated Cellulose Membrane According to the Present Invention with Cellufine™ Sulfate Gel MOCK cells from ECACC, UK, Nr. 841211903 are initially grown in roller bottles (Greiner, Germany, 850 cm$^2$) containing 250 ml GMEM basal medium (Invitrogen/Gibco, #22100-093) supplemented with FCS. After the cells reach confluency they are washed with PBS, trypsinized and applied as an inocculum ((2-3)×10$^5$ cells/all) for a 5 l bioreactor (B. Braun Biotech) containing the same media and 2.0 g/l Cytodex 1 solid microcarriers (Amersham Biosciences). The cells are cultivated under standard conditions for 4 days, washed with PBS and infected with Influenza virus (either A Puerto Rico/8/34, H1N1 (NIBSC #99-716), A/Wisconsin/67/2005, H3N2 (NIBSC #06/112) or B/Malaysia/2506/2004 (NIBSC #06/104)) at a MOI of 0.025. The infected cultures are maintained for 48 to 72 h in virus maintenance medium under standard conditions as described in Genzel et al., Vaccine, 2004, 22, 2202-2208. After cultivation, cells and microcarriers as well as cell agglomerates are separated from the medium by sedimentation. The cultivation broth are than clarified by a combination of two filters (pore size: 5 and 0.65 μm, GE Water & Process Technologies) and subjected to chemical inactivation with 3 mM β-propiolactone (Serva Electrophoresis) for 24 h at 37° C. The inactivated broths are again clarified by a 0.45 μm membrane filter (GE Water & Process Technologies) and approximately 20-fold concentrated by a cross flow ultrafiltration (750 kDa; GE-Healthcare).

The concentrates are loaded to a 3 ml Cellufine™ sulphate (Chisso Corporation) column (Tricorn5/150; GE-Healthcare) with a flow rate of 0.5 ml/min in phosphate buffer containing 50 mM NaCl at room temperature. The virus is eluted after a column wash (phosphate buffer containing 50 mM NaCl) with 0.6 M NaCl in PBS at room temperature. Further adsorbed contaminants are eluted with 2 M NaCl in PBS at room temperature The concentrates are loaded to 10 layers of the sulphated reinforced cellulose membranes in a stainless steel membrane holder (Whatman) with a flow rate of 0.5 ml/min in phosphate buffer containing 50 mM NaCl at room temperature. The virus is eluted after an adsorber wash (phosphate buffer containing 50 mM NaCl) with 0.6 M NaCl in PBS at room temperature. Further adsorbed contaminants are eluted with 2 M NaCl in PBS at room temperature.

In addition the concentrates are loaded to 10 layers of the sulphated reinforced cellulose membranes in a stainless steel membrane holder (Whatman) with a flow rate of 15 ml/min in phosphate buffer containing 50 mM NaCl at room temperature. The virus is eluted after an adsorber wash (phosphate buffer containing 50 mM NaCl) with 0.6 M NaCl in PBS with a flow rate of 0.5 ml/min at room temperature. Further adsorbed contaminants are eluted with 2 M NaCl in PBS at room temperature.

TABLE 2

Purification efficiency comparison of sulphated reinforced cellulose membranes (flow rate 0.5 ml/min) with a cellufine ™ sulphate chromatography column (flow rate 0.5 ml/min) for influenza virus A Puerto Rico/8/34, A/Wisconsin/67/2005 and B/Malaysia/2506/2004 (LOQ - limit of quantification)

|  | double stranded DNA | | HA activity | | total protein content | |
| --- | --- | --- | --- | --- | --- | --- |
|  | Cellufine ™ sulphate | sulphated membrane adsorber | Cellufine ™ sulphate | sulphated membrane adsorber | Cellufine ™ sulphate | sulphated membrane adsorber |
| A/Puerto Rico/8/34 | | | | | | |
| Concentrate | 100 | 100 | 100 | 100 | 100 | 100 |
| Flow through | 38.9 | 50.2 | 38.9 | 21.4 | 46.5 | 49.1 |
| Eluted product | 23.5 | 10.1 | 56.6 | 81.6 | 17.6 | 16.4 |
| Further elution | 22.4 | 23.2 | 1.8 | 1.5 | LOQ | 4.7 |
| Summation | 84.8 | 83.5 | 97.3 | 104.5 | 64.1 | 70.2 |
| A/Wisconsin/67/2005 | | | | | | |
| Concentrate | 100 | 100 | 100 | 100 | 100 | 100 |
| Flow through | 82.9 | 76.5 | 0 | 0 | 38.6 | 48.5 |
| Eluted product | 8.9 | 31.9 | 99.4 | 94.2 | 62.7 | 42.9 |
| Further elution | 1.3 | 2.5 | 0.0 | 2.2 | LOQ | LOQ |
| Summation | 93.1 | 110.9 | 99.4 | 96.4 | 101.3 | 91.4 |
| B/Malaysia/2506/2004 | | | | | | |
| Concentrate | 100 | 100 | 100 | 100 | 100 | 100 |
| Flow through | 98.1 | 90.7 | 75.4 | 23.4 | 38.4 | 36.6 |
| Eluted product | 0.2 | 1.0 | 30.7 | 72.9 | 38.8 | 41.8 |
| Further elution | 0.0 | 0.3 | 0.5 | 1.6 | LOQ | LOQ |
| Summation | 98.3 | 92.0 | 106.6 | 97.9 | 77.2 | 78.4 |

TABLE 3

Purification efficiency using sulphated reinforced cellulose membranes at two different flow rates (0.5 ml/min and 15 ml/min) for influenza virus A Puerto Rico/8/34 (LOQ - limit of quantification)

|  | double stranded DNA | | HA activity | | total protein content | |
| --- | --- | --- | --- | --- | --- | --- |
| A/Puerto Rico/8/34 | 0.5 ml/min | 15 ml/min | 0.5 ml/min | 15 ml/min | 0.5 ml/min | 15 ml/min |
| Concentrate | 100 | 100 | 100 | 100 | 100 | 100 |
| Flow through | 50.2 | 65.4 | 21.4 | 22.3 | 49.1 | 59.5 |
| Eluted Product | 10.1 | 4.5 | 81.6 | 61.8 | 16.4 | 14.7 |
| Further elution | 23.2 | 12.1 | 1.5 | 1.6 | 4.7 | LOQ |
| Summation | 83.5 | 82.0 | 104.5 | 85.7 | 70.2 | 74.2 |

From the table above, it is clear that compared to the Cellufine™ sulfate gel, the sulfated reinforced cellulose membrane results in higher productivity. It is possible, to run the purification with higher possible flow rate with increased maximum pressure.

The increased flow rates results in a double stranded DNA reduction, that is a reduction of host cells DNA. This is clear from the date above, when comparing the sulfated reinforced membrane results obtained with a flow rate of 15 ml/min against the results obtained with a flow rate of 0.5 ml/min. A reduction of 50% is achieved. Moreover, compared to the prior art gel Cellufine™ sulfate the content of double stranded DNA can be reduced from 23.5% to 4.5% in the product fraction. Furthermore, the HA activity is significantly increased when using the sulfated cellulose reinforced membrane according to the present invention while the total protein content is not significantly affected.

As shown above, the use of the sulfated cellulose membrane according to the present invention is suitable for various types of influenza virus, in particular, for the purification of whole virus suitable for the production of vaccines.

Example 7

Isolation of Vaccinia Ankara Virus

Production of Modified Vaccinia Ankara Virus Particles

MVA-BN® virus particles were produced by Bavarian Nordic A/S (Denmark) in primary cultures of CEF cells under Good Manufacturing Practice conditions. The starting material for this study was provided after homogenization and clarification as a liquid frozen product, stored in aliquots at −20° C. or −80° C. The TCID50 values of the samples were provided by Bavarian Nordic A/S.

MVA-BN®-Quantification

Virus titers were determined in triplicates by a sandwich ELISA. The relative virus amounts were correlated to the initial TCID50 value. As capturing antibody a rabbit anti-Vaccinia virus (Cat. #220100717; Quartett Immunodiagnostika & Biotechnologie GmbH, Germany) was used. The detection antibody was a peroxidase conjugated polyclonal rabbit anti-Vaccinia virus antibody (Cat. #8104; ViroStat, USA).

Total Protein Assay

Total protein concentrations were determined in triplicates by the Pierce® BCA protein assay reagent kit (Cat. #23225; Pierce Biotechnology, USA) according to the manufacture's instructions. The assay was calibrated against albumin standards (BSA) (Cat. #23209; Thermo Fisher Scientific Inc., USA) within the validated working range of 25 to 250 μg/ml (limit of detection: 8.3 μg/ml; limit of quantification: 25 μg/ml) using 100 mM citric acid and 250 mM NaCl buffer pH 7.2 for dilutions. All samples were adjusted to the same buffer conditions.

dsDNA-Assay

The dsDNA measurements were done using the Quant-iT™ PicoGreen® dsDNA reagent from Molecular Probes, Inc. (Cat. #P7581, USA). The assay was calibrated against lambda DNA (Cat. #D1501, Promega Corporation, USA) within the validated working range of 4 to 1000 ng/ml (weighted regression; limit of detection: 0.66 ng/ml; limit of quantification: 2.36 ng/ml) using 100 mM citric acid buffer pH 7.2 for dilutions. The same buffer was used for sample preparation via dialysis (5000 kDa MWCO; Cat. #131192, Spectrum Europe B.V., Netherlands) and sample dilutions. After incubation of standards and samples with the reagent, the fluorescent signal was measured at an emission and excitation wavelength of 535 nm and 485 nm, respectively (Mithras LB 940, Berthold Technologies GmbH & Co. KG, Germany). All samples were measured in duplicates.

Chromatography Materials

Pseudo-affinity membrane adsorbers—Heparin-MA was a research product of Sartorius Stedim Biotech GmbH, Germany. It was based on reinforced stabilized cellulose with a pore size>3 μm and an adsorption area of 3×75 cm2 by 3×15 layers. The housing material was polypropylene. Sulfated cellulose MA (SC-MA) according to the present invention with a diameter of 25 mm (pore size>3 μm, Sartorius Stedim Biotech GmbH, Germany) were prepared as described above. The adsorption area was 75 cm2 and 15 membranes were stacked in a stainless steel membrane holder (Cat. #1980-002, GE Healthcare, Germany).

Ion exchange membrane adsorbers—Dynamic binding capacity studies and capturing experiments (where applicable) were conducted by four different ion exchange MA: A strong anion exchange MA (Sartobind Q75-MA; Cat. #Q75X; 75 cm2, 15 layers), a weak anion exchange MA (Sartobind 075-MA; Cat. #D75X; 75 cm2, 15 layers), a strong cation exchange MA (Sartobind S75-MA; Cat. #S75X; 75 cm2, 15 layers) and a weak cation exchange MA (Sartobind C75-MA; Cat. #C75X; 75 cm2, 15 layers). All ion exchange MA were from Sartorius Stedim Biotech GmbH, Germany.

Bead-based pseudo-affinity resins—Cellufine® sulfate (3 ml, Cat. #19845, Chisso Corporation, Japan), and Toyopearl AF-Heparin HC-650M (3 ml, Cat. #20030, Tosoh Bioscience, Germany) were packed into a Tricorn 5/150 column (GE Healthcare, Germany).

Adsorption Chromatography

Chromatography was performed using an Akta Explorer system (GE Healthcare, Germany) at a flow rate of 0.5 ml/min (unless stated differently) and monitored by UV (280 nm) and light scattering (90°, Dawn EOS, Wyatt Technology Inc., USA) detection.

Dynamic binding capacity of the chromatography media was determined loading the clarified MVA-BN® virus sample (4.65×107 TCID50/ml) at a flow rate of 0.5 ml/min is onto Sartobind S75-MA, C75-MA, Q75-MA, D75-MA, Heparin-MA and SC-MA. All applied MA had a surface area of 75 cm2 and were composed of 15 layers. In parallel, the dynamic binding capacity was determined for the 3 ml Cellufine® sulfate and Toyopearl® AF-Heparin beads. The breakthrough was monitored via light scattering detector.

Characterization of the chromatography materials was done with 4 ml of the clarified MVA-BN® virus sample, representing a dynamic binding capacity of approximately 49% for the C75-MA (3×75 cm2), 22% for the heparin-MA (3×75 cm2) and less than 20% for the Q75-MA (75 cm2), D75-MA (75 cm2), SC-MA (75 cm2) and the 3 ml Cellufine® sulfate column. Prior to sample loading the chromatography material was equilibrated with sample buffer (100 mM citric acid, pH 7.2). After a brief washing the adsorbed virus particles were eluted with elution buffer (100 mM citric acid, 2 M NaCl, pH 7.2). Resulting fractions were pooled and analyzed for virus and contaminant compositions. Chromatographic materials were regenerated after each run with 10 column volumes of 1 M NaOH and 0.1 M HCl in 1 M NaCl. Dynamic binding studies were performed in triplicates for Cellufine® sulfate and the heparin-MA and once for all other materials (Table 4). All other experiments were performed at least in triplicates.

Combination of Membrane Adsorbers

The chromatography was performed using the same system and monitored as described above. All membrane adsorbers were equilibrated with sample buffer (100 mM citric acid, pH 7.2) before virus adsorption. Six ml of the clarified MVA-BN® virus sample were subjected to a SC-MA (75 cm2) or a heparin-MA (225 cm2) at a flow rate of 10 ml/min. After a brief washing (sample buffer, 10 ml/min) the adsorbed virus particles were eluted (100 mM citric acid, 2 M NaCl, pH 7.2; 0.5 ml/min), pooled and dialysed against sample buffer with a MWCO of 5000 kDa (Cat. #131192, Spectrum Europe B.V., Netherlands). Dialysed samples were further purified via a Q75-MA (75 cm2) applying identical operating conditions as for the pseudo-affinity MA, except for the adsorption flow rate of 0.5 ml/min.

The virus content and the amount of total dsDNA and protein were determined from a representative sample as described above. Analytical samples removed were considered in the overall mass balances.

Results

Separation of MVA-BN® by membrane adsorption chromatography and Cellufine® sulfate column chromatography Based on an overall pI of approximately 4 of intact Vaccinia virus particles, anion exchange matrices represent a favourable matrix for purification of Vaccinia virus particles. This was confirmed during the characterization of the ion exchange MA and by the dynamic binding capacity studies. Both tested anion exchange MA (Q75-MA and D75-MA) had a dynamic binding capacity of >20 ml culture broth capturing MVA-BN® virus particles (Table 4).

TABLE 4

Dynamic binding capacity of the tested chromatography materials.

| Chromatography Media | Functional Groups | N | Breakthrough Volume (ml) | Total TCID$_{50}$ (TCID$_{50}$) |
|---|---|---|---|---|
| Q75-MA | Quaternary ammonium | 3 | >20 | >9.3 × 10$^8$ |
| D75-MA | Diethylamine | 3 | >20 | >9.3 × 10$^8$ |
| S75-MA | Sulfonic acid | 3 | 2.5 | 1.2 × 10$^8$ |
| C75-MA | Carboxyl | 3 | 2.7 | 1.3 × 10$^8$ |
| Heparin-MA | Heparin | 3 | 6.0 | 2.8 × 10$^8$ |
| SC-MA | Sulfated cellulose (~20 μg/g dry membrane) | 3 | >20 | >9.3 × 10$^8$ |
| Toyopearl ® AF-Heparin (3 ml) | Heparin | 3 | 3.0 | 1.4 × 10$^8$ |
| Cellufine ® sulfate (3 ml) | Sulfated cellulose (≧700 μg/g dry gel) | 3 | >20 | >9.3 × 10$^8$ |

The adsorption area of all membrane adsorbers was 75 cm$^2$. The applied buffer was 100 mM citric acid (pH 7.2).

Comparable dynamic binding capacities (>20 ml) were achieved by the sulfated cellulose based pseudo-affinity matrices (SC-MA and 3 ml Cellufine® sulfate column). A reduced capacity of 6.0 ml and 3.0 ml was observed for the heparin matrices, the heparin-MA and the 3.0 ml Toyopearl AF-Heparin column, respectively. The tested cation exchange MA, S75-MA and C75-MA, resulted in a dynamic binding capacity of 2.5 ml and 2.7 ml, respectively.

The main advantage of MA, either SC-MA or Heparin-MA, compared to conventional column chromatography for purification of large components (i.e. virus particles) is the reduced pressure drop, allowing operations at higher flow rates. In the case of affinity MA processes, the flow rate is mainly limited by the association and dissociation kinetics of the ligand-target complex. As shown in Table 5, an increase in flow rate from 0.5 ml/min to 10 ml/min resulted in a minimal decrease in virus recovery for the SC-MA (14%) and heparin-MA (12%) with a total virus recovery in the product fraction of 51% and 47%, respectively. The amount of dsDNA in the product fraction at 10 ml/min was slightly reduced compared to 0.5 ml/min for both adsorbers (Tab. 5).

TABLE 5

Effect of increased flow rates on viral recovery and contaminant depletion.

| Flow Rate (ml/min) | Membrane Adsorber | MVA-BN ® (%) | dsDNA (%) | Total Protein (%) |
|---|---|---|---|---|
| 0.5 | Cellufine ® sulfate | 59 ± 5.7 | 7.0 ± 1.9 | 0.2 ± 0.2 |
| 0.5 | SC-MA | 65 ± 0.5 | 6.0 ± 0.2 | <LOQ$^a$ |
| 5.0 | SC-MA | 54 ± 0.3 | 4.0 ± 1.0 | <LOQ$^a$ |
| 10.0 | SC-MA | 51 ± 0.2 | 4.0 ± 0.7 | <LOQ$^a$ |
| 0.5 | Heparin-MA | 59 ± 1.3 | 17 ± 2.1 | <LOQ$^a$ |
| 5.0 | Heparin-MA | 47 ± 3.9 | 11 ± 0.3 | <LOQ$^a$ |
| 10.0 | Heparin-MA | 47 ± 0.4 | 9 ± 3.1 | <LOQ$^a$ |

Relative amounts (mean and standard deviation of triplicates) for MVA-BN ® (ELISA), dsDNA and total protein content were calculated based on the starting material of the homogenized and clarified virus broth. The adsorption area of the SC-MA and heparin-MA was 75 cm$^2$ and 225 cm$^2$, respectively. Equilibration and wash buffer was 100 mM citric acid (pH 7.2), and the elution buffer 100 mM citric acid + 2 M NaCl (pH 7.2).
$^a$limit of quantification (25 μg/ml)

The recommended operating pressure (manufacture's instruction) for Cellufine® sulfate is less than 2 bar. For the applied set-up, as described in the material and methods section, this limited the flow rate to 0.5 ml/min for bead-based separations. A change in column dimensions would have allowed an increase in the flow rate for Cellufine® sulfate. However, wide column dimensions at a constant matrix volume lead to a reduced residence time, resulting in potential product losses. On the other hand, up-scaling of the complete matrix volume has to be questioned in terms of the process economics.

Summing up, the overall performance based on capacity, purity, virus yield and productivity of the SC-MA was significantly better compared to ion exchange MA and heparin-MA. In terms of productivity the SC-MA can clearly be favoured over the bead-based Cellufine® sulfate as it is possible to increase the flow rates 20-fold for the SC-MA chromatography.

The combination of the different membrane absorbers allows to teduce the amount od dsDNA in the product significantly. That is, the the amount of dsDNA in the product fraction was reduced to 0.1% and 5% respectively. The overall virus recovery for the SC-MA and heparin-MA set-up was 58% and 59%, respectively. Moreover, after introduction of the subsequent anion exchange MA protein contaminations in the product fractions were reduced below the quantification limit (5 μg/ml) for both purification schemes.

CONCLUSIONS

Pseudo-affinity MA allowed the capture of CEF cell-derived MVA-BN® at a high loading velocity (10 ml/min) with a relatively high purity. Compared to the bead-based pseudo-affinity matrix Cellufine® sulfate (0.5 ml/min), productivity could be increased by a factor of 20 with a slightly reduced product yield. The achieved purity levels, in particular the dsDNA depletion, were significantly higher for the pseudo-affinity matrices than for the tested ion exchange.

The invention claimed is:
1. A method for the preparation of sulfated cellulose membranes, comprising the steps of:
   a) adding chloro-sulfonic acid to pyridine at a temperature below or equal to 0° C. to form a mixture;
   b) reacting said mixture at a temperature of 60° C. or above to form a reactant mixture;

c) cooling the reactant mixture at a temperature of 40° C. or below;
d) adding cellulose membrane to said reactant mixture and
e) reacting the cellulose membrane and reactant mixture at a temperature of 40° C. or below to obtain a sulfated cellulose membrane, wherein said sulfated cellulose membrane has a degree of sulfation of the cellulose in a range from 0.5 to 15%, in a reaction mixture.

2. The method according to claim 1, wherein the cellulose membrane added to said reactant mixture is a regenerated cellulose membrane.

3. The method according to claim 1, further comprising the step of f.) cooling the reaction mixture to ambient temperature.

4. The method according to claim 3 further comprising the step of g.) neutralizing the reaction mixture with a base.

5. The method according to claim 4 further comprising the step of h.) washing the sulfated cellulose membrane with phosphate buffered saline solution.

6. The method according to claim 1 wherein the mixture is reacted at a temperature of from 60° C. to 80° C.

7. The method according to claim 1 wherein the reactant mixture is cooled to a temperature in the range of from 40° C. to 10° C.

8. The method according to claim 1, wherein the temperature for reacting the cellulose membrane with the reactant mixture is in the range of from 35° C. to 20° C.

9. The method according to claim 1 wherein the reactant mixture is cooled to a temperature in the range of from 35° C. to 30° C.

10. Sulfated cellulose membrane made by the process of:
adding chloro-sulfonic acid to pyridine at a temperature below or equal to 0° C. to form a mixture; reacting said mixture at a temperature of 60° C. or above to form a reactant mixture;
cooling the reactant mixture at a temperature of 40° C. or below;
adding cellulose membrane to said reactant mixture and reacting the same at a temperature of 40° C. or below to obtain a sulfated cellulose membrane, wherein said sulfated cellulose membrane has a degree of sulfation of the cellulose in a range from 0.5 to 15%.

11. The membrane according to claim 10, wherein the cellulose membrane is made from a regenerated cellulose.

12. A method for isolating proteinaceous compositions comprising the step of using a sulfated membrane for isolation of proteinaceous compositions, wherein said sulfated membrane is made by the process of:
adding chloro-sulfonic acid to pyridine at a temperature below or equal to 0° C. to form a mixture;
reacting said mixture at a temperature of 60° C. or above to form a reactant mixture;
cooling the reactant mixture at a temperature of 40° C. or below;
adding cellulose membrane to said reactant mixture; and
reacting the cellulose membrane and reactant mixture at a temperature of 40° C. or below to obtain a sulfated cellulose membrane, wherein said sulfated cellulose membrane has a degree of sulfation of the cellulose in a range from 0.5 to 15%, wherein said sulfated membrane isolates proteins in a proteinaceous composition.

13. The method according to claim 12, wherein the proteinaceous compositions are whole virus.

14. The method according to claim 12, wherein the proteinaceous composition is a composition of virus proteins and/or non-virus proteins.

15. The method according to claim 12, wherein the proteinaceous composition is influenza or vaccinia virus or proteinaceous fragments thereof.

16. A method for isolating whole virus or virus proteins comprising the step of using sulfated cellulose membrane for affinity purification of a composition containing whole virus or virus proteins wherein said using sulfated cellulose membrane is made by the process of:
adding chloro-sulfonic acid to pyridine at a temperature below or equal to 0° C. to form a mixture;
reacting said mixture at a temperature of 60° C. or above to form a reactant mixture;
cooling the reactant mixture at a temperature of 40° C. or below;
adding cellulose membrane to said reactant mixture; and
reacting the cellulose membrane and reactant mixture at a temperature of 40° C. or below to obtain a sulfated cellulose membrane, wherein said sulfated cellulose membrane has a degree of sulfation of the cellulose in a range from 0.5 to 15%, wherein said sulfated membrane isolates one or more of whole virus or virus proteins.

17. The method according to claim 16, wherein whole virus is isolated.

18. A method for isolating heparin binding molecules comprising the step of pseudo-affinity purification using sulfated cellulose membranes made by the process of:
adding chloro-sulfonic acid to pyridine at a temperature below or equal to 0° C. to form a mixture;
reacting said mixture at a temperature of 60° C. or above to form a reactant mixture;
cooling the reactant mixture at a temperature of 40° C. or below;
adding cellulose membrane to said reactant mixture; and
reacting the same at a temperature of 40° C. or below to obtain a sulfated cellulose membrane, wherein said sulfated cellulose membrane has a degree of sulfation of the cellulose in a range from 0.5 to 15%,
said sulfated cellulose membrane isolating heparin binding molecules during pseudo-affinity purification.

* * * * *

UNITED STATES PATENT AND TRADEMARK OFFICE
CERTIFICATE OF CORRECTION

PATENT NO. : 8,173,021 B2  
APPLICATION NO. : 12/580413  
DATED : May 8, 2012  
INVENTOR(S) : Wolff et al.

Page 1 of 1

It is certified that error appears in the above-identified patent and that said Letters Patent is hereby corrected as shown below:

ON THE TITLE PAGE:  
Please insert the following:  
Item -- (30)  Foreign Application Priority Data  
            April 17, 2007  (EPO)  07007759.9  
            April 17, 2008  (PCT)  EP2008/003093

(60) Provisional Application No. 60/912,305, filed April 17, 2007 --

IN THE SPECIFICATIONS:  
Column 1, after the title, and before line 5, insert the following heading and paragraph:

-- RELATED APPLICATION DATA

This application is a CIP of PCT/EP2008/003093 filed April 17, 2008 which claims benefit of U.S. Provisional Application No. 60/912,305 filed April 17, 2007. --

Signed and Sealed this  
Second Day of October, 2012

David J. Kappos  
*Director of the United States Patent and Trademark Office*